(12) United States Patent
Buthe et al.

(10) Patent No.: US 8,226,967 B2
(45) Date of Patent: Jul. 24, 2012

(54) SURFACE ACTIVE PROTEINS AS EXCIPIENTS IN SOLID PHARMACEUTICAL FORMULATIONS

(75) Inventors: Andreas Buthe, Steinfurt (DE); Andreas Hafner, Gelterkinden (CH); Franz Kaufmann, Freiburg (DE); Esther Gabor, Zwingenberg (DE); Guido Meurer, Seeheim-Jugenheim (DE); Jürgen Eck, Heppenheim (DE); Gordon Bradley, Liestal (CH)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/130,128

(22) PCT Filed: Nov. 13, 2009

(86) PCT No.: PCT/EP2009/065100
§ 371 (c)(1), (2), (4) Date: Jul. 19, 2011

(87) PCT Pub. No.: WO2010/060811
PCT Pub. Date: Jun. 3, 2010

(65) Prior Publication Data
US 2011/0268792 A1    Nov. 3, 2011

(30) Foreign Application Priority Data
Nov. 27, 2008  (EP) .................... 08170101

(51) Int. Cl.
*A01N 25/34* (2006.01)
*C07K 1/00* (2006.01)

(52) U.S. Cl. ........................ 424/408; 530/350
(58) Field of Classification Search .......... 530/350; 424/408
See application file for complete search history.

(56) References Cited

U.S. PATENT DOCUMENTS

| | | | |
|---|---|---|---|
| 4,859,469 A | 8/1989 | Baudier |
| 5,407,686 A | 4/1995 | Patel |
| 5,538,738 A | 7/1996 | Ritter |
| 6,238,698 B1 | 5/2001 | Cremer |
| 2003/0113454 A1 | 6/2003 | De Vocht |
| 2003/0217419 A1 | 11/2003 | Gabin |
| 2005/0238685 A1 | 10/2005 | Hektor |
| 2006/0040098 A1 | 2/2006 | Imbalzano |
| 2007/0087022 A1 | 4/2007 | Desai |
| 2009/0041922 A1 | 2/2009 | Kuhnle et al. |
| 2009/0136433 A1 | 5/2009 | Subkowski et al. |
| 2010/0143484 A1 | 6/2010 | Beco Pinto Reis et al. |
| 2010/0166627 A1 | 7/2010 | Baus et al. |
| 2010/0170142 A1 | 7/2010 | Posselt et al. |
| 2010/0240774 A1 | 9/2010 | Subkowski |
| 2011/0159050 A1 | 6/2011 | Hafner et al. |

FOREIGN PATENT DOCUMENTS

| | | |
|---|---|---|
| EP | 1350507 A | 10/2003 |
| WO | 9641882 A1 | 12/1996 |
| WO | 9942086 A1 | 8/1999 |
| WO | 0071079 A | 11/2000 |
| WO | 2004062560 A2 | 7/2004 |
| WO | 2005068087 * | 7/2005 |
| WO | 2006010921 A1 | 2/2006 |

OTHER PUBLICATIONS

Copending U.S. Appl. No. 11/887,282, filed Aug. 17, 2007.
Lumsdon et al., Colloids and Surfaces. B, Biointerfaces, Elsevier, vol. 44, No. 4, pp. 172-178 (Sep. 1, 2005).
Haas et al., Colloids and Surfaces. B, Biointerfaces, Elsevier, vol. 75, No. 2, pp. 526-531 (Feb. 1, 2010).
Cox et al., Food Hydrocolloids, Elsevier, vol. 23, No. 2, pp. 366-376 (Mar. 1, 2009).

\* cited by examiner

*Primary Examiner* — Maryam Monshipouri
(74) *Attorney, Agent, or Firm* — Tyler A. Stevenson

(57) ABSTRACT

The invention relates to a use of surface active hydrophobins for applications in pharmaceutical technology, in particular as excipients for galenic use. Provided is a method for either admixture of hydrophobins to galenic compositions or for treating the surface of pharmaceutical forms with a hydrophobin-containing solution to modify the pharmaceutical properties of the galenic form. In a preferred embodiment of the invention hydrophobins are used to improve the properties of a pharmaceutical composition, e.g. to act as a surfactant or to increase resistance to disintegration of the galenic forms to achieve a retarded drug release. The galenic form to be modified by the use of surface active proteins as excipients can be capsules, tablets, pills, microparticles, vesicles, and suppositories, although further galenic forms are envisioned. The surface active proteins used for the purpose of present invention can either be isolated from their respective natural source or prepared by recombinant techniques and expression in a suitable host.

14 Claims, 5 Drawing Sheets

A release kinetics from gelatine capsules at pH 1.0

B release kinetics from gelatine capsules at pH 1.0 + 0.4 U/ml pepsin

A release kinetics from alginate capsules at pH 1.0

B release kinetics from alginate capsules at pH 1.0 + 0.4 U/ml pepsin

A

B

C

A

B without hydrophobin with hydrophobin SC3

SURFACE ACTIVE PROTEINS AS EXCIPIENTS IN SOLID PHARMACEUTICAL FORMULATIONS

This application is a 371 of PCT/EP2009/065100 filed Nov. 13, 2009, which claims priority to European Patent Application No. 08170101.3, filed Nov. 27, 2008.

The present invention pertains to the use of surface active proteins selected from hydrophobins, preferably fungal hydrophobins, as excipients for the formulation of pharmaceutical compositions. One major object of the invention is the use of surface active proteins in galenic applications to modulate stability and release characteristics of a drug in an advantageous way. A use of surface active proteins according to the invention is the formulation of by admixture of the surface active proteins to the galenic composition or by modifying the pharmaceutical form by coating or incorporation into or formation of a matrix.

TECHNICAL BACKGROUND

Optimisation of galenic forms plays an important role in the formulation of medicaments to achieve adequate pharmaceutical properties such as optimal drug release and convenience for the patient. For the preparation of a pharmaceutical composition capsules (*Capsulae medicinales*) are frequently used. The shell of the capsules often consists of biopolymers such as gelatine, starch or other suitable pharmaceutically inert matter like dried gels of macromolecular substances. The capsules are soluble, digestible or permeable under physiological conditions in vivo. Due to a number of advantageous properties capsules are frequently used to formulate solid, semisolid or liquid drugs: (a) even sensitive and technologically problematic pharmaceutical compositions can be formulated, (b) the drugs are protected from environmental hazards (light, air, humidity), (c) expiry date and shelf-life are increased, (d) high dosage reliability especially of liquid drugs, (e) optimal and ensured drug release characteristics (with or without sustained release effect), (f) convenient application with neutral taste and smell, (g) well tolerated, (h) unambiguous identification by shape, colour and imprint implying an increased drug safety. One problem with the use of orally applied capsules is the controlled release during the passage through stomach and intestine. Resistance to stomach acids to different degree can be achieved by coating with cellulose acetate phtalate, hydroxypropyl methyl cellulose phtalate or a varnish of acrylic resins.

Another galenic form for oral administration of drugs is the use of a matrix which is resistant to disintegration for the formulation of tablets. The matrix consists of e.g. cellulose ether or crosslinked amylose, as disclosed in U.S. Pat. No. 6,238,698 for tablets comprised of several layers including a matrix layer and an excipient layer which increases the resistance of the matrix layer to disintegration. U.S. Pat. No. 5,407,686 discloses a composition for the construction of a tablet consisting of multiple layers, one of which is a film coating comprising a soluble polymer and a plasticizer. Further galenic forms like microgranules, micelles or vesicles have been disclosed, some of them reporting increased resistance to degradation or sustained release.

The use of the surface active proteins of the present invention as novel excipients may contribute significantly to the improvement of these galenic forms in the preparation of e.g. matrix tablets, aerosols, suspensions or liquid medicines.

U.S. Pat. No. 5,538,738 describes a system providing sustained release of medicinal or biological material by admixture of hydroxycarboxylic acids to a dosage form to modify retard systems or depot materials. WO 99/042086 proposes a prolonged release galenic form comprising an absorption-promoting agent based on lipid substances. U.S. Pat. No. 4,859,469 discloses novel galenic forms comprising microgranules being coated with a microporous membrane consisting of a synthetic polymer and a pharmacologically acceptable adjuvant.

None of the above patents describes the use of surface active proteins like for example hydrophobins, chaplins, curlins or latherin, as surface active excipients in the preparation of pharmaceutical forms. The present invention therefore provides a means of endowing polymers with advantageous acid-resistant and prolonged-release characteristics properties, i.e. for a variety of galenic uses as outlined above. Envisioned is the admixture of surface active proteins within the process of preparation of polymers or the coating of polymers for pharmaceutical use. The most prominent advantage is that the passage of drugs in the galenic form according to the present invention through the stomach is allowed, when drug release mainly in the intestine is indicated or even a controlled release in the intestine is desired.

Surface active agents can change the chemical and physical properties of the interface when such agents are adsorbed onto the surfaces of dispersed particles. Amphiphilic surface active agents consist of hydrophobic and hydrophilic segments. The hydrophobic part will adsorb on a non-polar surface or be attracted by a non-polar phase whereas the hydrophilic segment will be attracted to a polar surface or phase. Such surface active agents can thus be used to make hydrophilic surfaces hydrophobic and hydrophobic surfaces hydrophilic. Certain surface active agents can self-assemble at any hydrophilic-hydrophobic interface into an amphipathic film. Such self-assembly can significantly improve the properties of a (bio)polymer. At liquid/water interfaces, surface active agents reduce the water surface tension which results in a change of the contact angle of a water-droplet. This parameter can be used for the measurement of the activity of a surface active agent. The use of surface active agents can contribute significantly to the improvement of galenic forms in the preparation and performance of e.g. capsules, pills, tablets, microgranules and suppositories.

Some proteins of natural origin act as surface active agents. Surface active proteins comprise, but are not limited to, hydrophobins, chaplins, curlins or latherin.

Hydrophobins are small cystein-rich fungal surface active proteins of about 10 kDa in size, which self-assemble at hydrophilic-hydrophobic surfaces or interfaces into highly insoluble amphipathic layers. They are characteristic of filamentous fungi, for example of *Schizophyllum commune* or *Trichoderma reesei* and are found as structural proteins on surfaces of aerial structures of fungi where the hydrophobic coating is proposed to have a protecting role both against desiccation, wetting and protecting the conidia of filamentous fungi against extreme environmental conditions. Two classes of hydrophobins have been distinguished based on aqueous solubility and hydropathy. Hydrophobins can be isolated from natural sources, but it is also possible for hydrophobins that do not occur naturally to be synthesised by means of chemical and/or biotechnological methods of preparation. The use of engineered SC3 to achieve surface modifications, namely wettability and enhanced growth of fibroblasts, has been described by Scholtmeijer, K. et al. (Surface modifications created by using engineered hydrophobins, Appl. Environ. Microbiol. 2002, 68(3): 1367-73).

EP1254158 describes a general method for coating a surface with hydrophobin. WO96/41882 proposes the use of hydrophobins as emulsifiers, thickeners or surface-active substances, for rendering hydrophobic surfaces hydrophilic, for improving the water resistance of hydrophilic substrates, and for preparing oil-in-water emulsions or water-in-oil emulsions.

Also proposed are pharmaceutical uses, such as the preparation of ointments or creams, and cosmetic uses, such as skin protection or the preparation of hair shampoos or hair conditioners (US2003/217419). Cosmetic uses are also proposed in WO 06/136607 where the binding properties of hydrophobins to keratin or to mucosa or teeth are utilized to direct cosmetic effector molecules, e.g. in the form of compositions or conjugates with a hydrophobin, to the desired site of action (hair, nails, skin). A method of binding a compound of interest (e.g. enzyme, antibody, nucleic acid) to a surface using a hydrophobin-like coating is described in WO04/00880.

However, the use of hydrophobins according to prior art is mostly related to the modification of surface properties by coating with a hydrophobin-containing solution. Apart from implementations as emulsifiers and thickeners stated above the use of hydrophobins or other surface active proteins as excipients in galenics has not been described to date.

SUMMARY OF THE INVENTION

The invention provides a method for utilising surface active proteins as excipients in pharmaceutical technology, particularly in galenics. In one preferred embodiment of the invention hydrophobins are utilised as galenic excipients for the formulation of pharmaceutical compositions in order to modulate the characteristics of drug release in vivo. The hydrophobins may be used either by admixture to pharmaceutically utilised polymers and compounds, by incorporation into/formation of a matrix or by coating of galenic forms to achieve a modulation of release kinetics. Particularly preferred is a pH-dependent performance of the hydrophobin-containing galenic form, allowing e.g. an increased resistance of the galenic form to acidic stomach juices and a sustained release of the drug in the alkaline environment of the intestine. The pharmaceutical form to be treated with the method according to the present invention can be designated for oral application or other routes of administration (e.g. rectal application). Examples for galenic forms according to the present invention are capsules, pills, tablets, matrix tablets, microgranules and suppositories, but not limited to these.

The class I hydrophobins used for the purpose of the preferred embodiment of the present invention detailed above show distinct properties with regard to environments of different pH (see FIG. 3). This allows the person skilled in the art to select a suitable hydrophobin for the galenic form to be modulated in an advantageous way. As an example, the hydrophobin TT1 renders capsules more resistant to a basic environment, which can be utilised for the preparation of suppositories with a retarded drug release (see FIG. 3c).

Hydrophobins can be utilised as excipients in the production of different galenic forms with sustained release of the formulated drug or an increased resistance to disintegration of the galenic form: capsules or suppositories can be composed of e.g. gelatine, starch, alginate or any other pharmaceutically acceptable polymer; microgranules of a drug composition can be coated with microporous membranes consisting of e.g. methacrylate acid methylesters; micelles, tablets or pills can consist of e.g. amylase and can be comprised of different layers, of which one layer (e.g. the excipient layer) is resistant to disintegration.

DETAILED DESCRIPTION OF THE INVENTION

The method of the invention will be described by the use of surface active proteins of microbial origin—namely hydrophobins—which are intended for application in humans and/or animals to provide an improved galenic form and administration. The improved galenic form can, amongst others, render the formulated pharmaceutical composition resistant to stomach juices, provide a sustained release in vivo, modulate the dissolution kinetics of tablets and capsules and thus potentially increase the bioavailability of active agents.

Surface active proteins are amphiphilic, possessing both hydrophobic and hydrophilic properties. Naturally occurring compounds of this class therefore have been termed as "nature's surfactants". A synonym to amphiphilic is "amphipathic".

Amphiphatic proteins can physically adsorb on the surface of a solid substance to form a surface possessing both hydrophobicity and hydrophilicity oriented in accordance with the wettability of the surface being treated.

If the surface is hydrophobic, the hydrophobic side of the coating is in contact with the hydrophobic surface being coated, and the outer surface of the coating is hydrophilic, thereby increasing the water wettability of the surface being coated.

The surface active properties of proteins onto substrates can be assessed by interfacial tension measurements, characterization of oil-in-water emulsions and contact angles with water. The amphiphilic protein useful in the present invention is characterized by strongly lowering the contact angle of water (WCA) on a hydrophobic surface (e.g. the surface of a polyolefin or a Teflon® surface). Specifically, a 1% b.w. aqueous solution or dispersion of the amphiphilic protein useful in the present invention often shows a contact angle on a polypropylen surface (specifically: PP homopolymer type HC115MO, Borealis, melt flow rate =4.0 g/10 min [230° C./2.16 kg]) which is lower than the contact angle observed for pure water by 20 degrees or more, preferably 30 degrees or more, more preferably 40 degrees or more, most preferably 45 degrees or more, and in some specific cases 50 degrees or more (see FIG. 4; all WCA measurements, and data mentioned, according to static sessile drop method). Preferred for use as surface active proteins in the present invention are hydrophobins, such as those of class I or class II. Hydrophobins useful in the present invention, as well as sources and properties thereof, are generally known (see publications mentioned further above), and are described inter alia in WO 96/41882 (see passage from page 1, line 14, to page 7, line 20, and examples 1 to 5); WO 03/10331 (see passage from page 1, line 4, to page 5, line 20); or WO 06/103230 (see passage from page 3, paragraph 6, to page 12, $3^{rd}$ line from bottom of page); the specific passages mentioned are hereby incorporated by reference.

"Hydrophobins" and the preparation thereof are known; suitable hydrophobins for the implementation of the present invention are, for example, those of WO 06/103230. It is also possible to employ fragments or derivatives thereof. It is further possible to employ modified hydrophobines, e.g. wherein several identical or different structures have been linked to each other (e.g. as dimers or trimers) and/or to one or more suitable polypeptide sequences which are not naturally occurring in a hydrophobin. Naturally occurring hydrophobins may be isolated from natural sources by suitable methods (see, by way of example, Wösten et. al., Eur. J. Cell Biol. 63, 122-129 (1994), or WO 96/41882). The preparation of hydrophobins may also be carried out by genetic engineering methods in which a nucleic acid sequence, especially a DNA sequence, coding for the hydrophobin in the context of this invention is inserted into a host organism that the desired protein is produced by gene expression of the nucleic acid sequence. The gene expression can be carried out either in a heterologous or in a homologous host strain. In general, such methods are known; corresponding disclosures can be found, for example, in WO 06/082251.

The composition used for the treatment according to the present invention comprises at least one hydrophobin and an aqueous solvent, for example a solvent of which is water or a mixture of water and a miscible solvent.

For the use of hydrophobins in accordance with the invention to prepare the modified polymers, the hydrophobins can be used in solvent-free form, preferably they are used in the form of formulations based on water or any other pharmaceutically acceptable solvent. It will be understood that mixtures of solvents can also be used. The nature of the solvent depends, for example, on the hydrophobin, the nature of the polymer to be treated and its use, and is chosen accordingly by the person skilled in the art.

To prepare the composition used in accordance with the invention, preferably an aqueous solution of the hydrophobins is used. Suitable solutions may be obtained during synthesis, isolation and/or purification of the hydrophobin(s). Alternatively, it is also possible for the hydrophobins initially to be isolated in solvent-free form, for example by freeze-drying, and to be formulated only in a second step.

The choice of hydrophobins for the implementation of the invention is not restricted. One hydrophobin or a plurality of different hydrophobins can be used.

The amount of the hydrophobins in the formulation may be determined by the person skilled in the art in accordance with the nature of the surface and/or the use. Relatively small amounts are often sufficient to achieve the desired effect, e.g. the desired change of surface properties. A concentration of the surface active protein of 0.01 to 10.0 mg/ml is common, with about 0.2 mg/ml (e.g. 0.2 to 2 mg/ml, or even 0.5 to 1 mg/ml) being especially preferred.

Examples for solid application forms of the invention are tablets, coated tablets, capsules, granules, suppositories, implants.|6|

Pharmaceutical ingredients (APIs) or drugs, which may be contained in the present solid application forms, include: Acarbose, acetylsalicylic acid, alfuzosin, aliskiren, ambrisentan, amlodipine, amoxicillin, anastrozole, apixaban, aprepitant, aripiprazole, atazanavir, atenolol, atomoxetine, atorvastatin, azithromycin, bazedoxifene, benazepril, bicalutamide, bisacodyl, budesonide, butylscopolamine, candesartan, capecitabine, carbamazepine, carisbamate, carvedilol, casopitant, celecoxib, cetirizine, chloroquine, cinacalcet, ciprofloxacin, clavulanic acid, clodronate, clonidine, clopidogrel, cyproterone acetate, dapoxetine, darunavir, dasatinib, deferasirox, dextromethorphan, diclofenac, dienogest, dipyridamole, docetaxel, donepezil, drospirenone, duloxetine, efavirenz, eletriptan, enalapril, entacapone, entecavir, enzastaurin, erlotinib, esomeprazole, eszopiclone, ethinylestradiol, etoricoxib, etravirine, everolismus, exemestane, fexofenadine, finasteride, fluoxetine, fluticasone, fluticasone propionate, fluvastatin, formoterol, ganciclovir, gefitinib, glimepiride, hydrocodone, ibandronic acid, ibuprofen, indinavir, ipratropium, irbesartan, lamotrigine, lansoprazole, lapatinib, letrozole, levonorgestrel, linezolid, lisinopril, losartan, maraviroc, meloxicam, metformin, methylphenidate, metoprolol, moxidectin, mycophenolic acid, naproxen, nateglinide, nevirapine, nicorandil, nifedipine, nilotinib, olanzapine, omeprazole, orlistat, oseltamivir, oxaliplatin, oxcarbazepine, paliperidone, pantoprazole, paracetamol, paroxetine, pioglitazone, pramipexole, pravastatin, pregabalin, quetiapine, rabeprazole, raloxifene, ramipril, reboxetine, risedronate sodium, rivaroxaban, rivastigmine, rizatriptan, rosiglitazone, ruboxistaurin, salmeterol, sildenafil citrate, simvastatin, sirolimus, sitagliptin, sorafenib, sumatriptan, sunitinib, surinabant, tadalafil, tamsulosin, tapentadol, telbivudine, telmisartan, terbinafine hydrochloride, teriflunomide, tiotropium, tolterodine, topiramate, vabicaserin hydrochloride, valaciclovir, valganciclovir, valsartan, vandetanib, vardenafil, varenicline, venlafaxine, vildagliptin, voriconazole, warfarin, ziprasidone, zolmitriptan, zolpidem.

Further drugs: acepromazine, amoxicillin, ampicillin, apramycin, benazepril, betamethasone, buscopan, carprofen, cefapirin, clenbuterol, clindamycin, cloxacillin, cyclosporine A, cyromazine, deracoxib, dichlorvos, dicyclanil, difloxacin, enrofloxacin, etodolac, fenbendazole, framycetin, furosemide, griseofulvin, hetacillin, hygromycin, imidacloprid, levamisole, levothyroxine, lufenuron, meloxicam, milbemycin oxime, monensin, moxidectin, narasin, nicarbazin, nitenpyram, oleandomycin, oxfendazole, oxyclozanide, paramectin, paromomycin, permethrin, phenylbutazone, praziquantel, procaine benzylpenicillin, procaine penicillin, pyrantel pamoate, spinosad, sulphadiazine, thiamethoxam, tiamulin, triamcinolone, triclabendazole, trimethoprim, tylosin.

More specifically, the invention includes, but is not limited to, the following embodiments:

1. Method for modulating the characteristics of drug release from a solid application form in vivo, especially in the stomach and/or intestine, which method comprises incorporation of a surface active protein into said application form, or coating said application form with the surface active protein.
2. Pharmaceutical composition comprising a solid application form, characterized in that it contains a surface active protein
3. Use of a surface active protein for modulating the characteristics of drug release from a solid application form in vivo, especially in the stomach and/or intestine.
4. Method or composition or use as described above, wherein the surface active protein is characterized in that a 1% b.w. aqueous solution or dispersion thereof lowers the contact angle on a polypropylene surface by 20 degrees or more relative to pure water.
5. Method, composition or use as described above wherein the surface active protein is a hydrophobin, such as a class II hydrophobin or especially a class I hydrophobin.
6. Method, composition or use as described above, wherein the interfacial properties of the surface of the galenic application form (especially tablet, capsule) with the strongly acid environment of the stomach and/or the alkaline environment of the intestine are altered.
7. Method, composition or use as described above, wherein the interfacial properties of the active ingredient(s) or one or more of the excipients of the galenic application form with the strongly acid environment of the stomach and/or the alkaline environment of the intestine are altered.
8. Method, composition or use as described above, which comprises protecting the active ingredient(s) against chemical breakdown by the gastric juices of the stomach and/or the alkaline environment of the intestine.
9. Method, composition or use as described above, further comprising one or more further pharmaceutically acceptable ingredients, especially selected from further surface active agents such as binders, biopolymers, flow aids, lubricants, disintegrants to ensure that the tablet breaks up in the digestive tract; sweeteners or flavours; colorants.
10. Method, composition or use as described above, wherein the solid application form is a galenic form selected from capsules, pills, tablets, matrix tablets, microgranules and suppositories.

11. Method, composition or use as described above, wherein the surface active protein modulates the characteristics of drug release, especially with delay thereof, in vivo, especially in the stomach and/or intestine.
12. Method, composition or use as described above, wherein the solid application form is in tablet form containing surface active proteins to modulate the characteristics of drug release in vivo especially in the stomach and/or intestine.
13. Method, composition or use as described above, wherein the solid application form is in multilayer tablet form containing surface active proteins to modulate the characteristics of drug release in vivo especially in the stomach and/or intestine
14. Method, composition or use as described above, wherein the solid application form is in capsule form containing surface active proteins to modulate the characteristics of drug release in vivo especially in the stomach and/or intestine.
15. Method, composition or use as described above, wherein the solid application form is in multi capsule form containing surface active proteins to modulate the characteristics of drug release in vivo especially in the stomach and/or intestine.
16. Method, composition or use as described above, whereby the galenic form releases the active ingredient through chemical processes such as hydrolysis and enzymatic attack in vivo especially in the stomach and/or intestine.
17. Method, composition or use as described above, whereby the galenic form releases the active ingredient through physical processes such as erosion and diffusion processes in vivo especially in the stomach and/or intestine.
18. Method, composition or use as described above, whereby the galenic form releases the active ingredient through a combination of both physical and chemical processes in vivo especially in the stomach and/or intestine.
19. Method, composition or use as described above, whereby the galenic form releases the active ingredient(s) in the stomach.
20. Method, composition or use as described above, whereby the galenic form releases the active ingredient(s) in the intestine.
21. Method, composition or use as described above, combining any of the above features mentioned under (1) to (20).

The hydrophobin-containing formulation may optionally comprise further components as known in the art (see, for example, Lehrbuch der Pharmazeutischen Chemie by Harry Auterhoff, Joachim Knabe and Hans-Dieter Höltje, 14$^{th}$ Ed. 1999, Wissenschaftliche Verlagsgesellschft mbH Stuttgart [ISBN 3-8047-1645-8], especially part D thereof); examples for such components include other excipients, additives and/or adjuvants. Examples of such components include surfactants, such as anionic, non-ionic, amphoteric and/or cationic surfactants, and (bio-)polymers, and/or components as listed below:

Binders, including starches, sugars, cellulose or modified cellulose such as hydroxypropyl cellulose, lactose, sugar alcohols like xylitol, sorbitol or maltitol;
binders are classified according to their application include solution binders (dissolved in a solvent such as water, alcohol); binders used in wet granulation processes (examples including gelatin, cellulose, cellulose derivatives, polyvinylpyrrolidone, starch, sucrose and polyethylene glycol); dry binders e.g. as part of a direct powder compression (DC) formula (examples include cellulose, methyl cellulose, polyvinylpyrrolidone, and polyethylene glycol).

Coatings, including cellulose (plant fiber) film coatings, synthetic polymers, shellac, corn protein zein or other polysaccharides, gelatin (especially for capsules); enteric coatings for the control of drug release rate and determining where the drug will be released in the digestive tract.

Disintegrants (expand and dissolve when wet causing the tablet to break apart in the digestive tract, releasing the active ingredients for absorption), including water uptake facilitators and tablet rupture promoters; examples are starch, cellulose, crosslinked polyvinyl pyrrolidone, sodium starch glycolate, sodium carboxymethyl cellulosemethycellulose.

Fillers/Diluents (inert, compatible with the other components of the formulation, non-hygroscopic, soluble, compactible, and preferably tasteless or pleasant tasting); examples are plant cellulose (pure plant filler, especially in tablets or hard gelatin capsules), dibasic calcium phosphate (especially in tablets), vegetable fats and oils (especially in soft gelatin capsules), lactose, sucrose, glucose, mannitol, sorbitol, calcium carbonate, magnesium stearate.

Commercial examples for such additional components include coating materials and formulation aids from the EUDRAGIT® (supplier: EVONIK), Kollicoat® and Kollidon® (supplier: BASF) series.

In accordance with the invention, objects are treated by bringing (the surface of) the object into contact with hydrophobin or with a composition comprising at least one hydrophobin, at least one solvent and optionally one or more further component(s), e.g. selected from surfactants and (bio-)polymers.

The phrase "bringing into contact" means, for example, generating a mixture of the material with hydrophobins or by spraying the entire article/object with or immersing it in the formulation. The temperature at which treatment is being accomplished is generally ambient temperature, however, elevated or decreased temperatures, e.g. from the range −5° C. to +40° C., are also applicable, depending on the temperature tolerance of the object to be treated. The duration of treatment is determined by the person skilled in the art and can be from about a second up to several hours. After treatment, the surface can be rinsed, for example with water, to remove excess treatment solution.

Exemplification of the invention by way of the examples, as described herein, does not imply any limitation of the teaching according to the invention. By way of said examples, there are disclosed combinations of elements which act according to the invention and which are applicable to other fields of application in the same manner. More particularly, the invention is applicable to a broad range of applications in pharmaceutical technology and specifically to galenic forms of pharmaceutical compositions to be released with advantageous release characteristics like sustained or pH-dependent release and modulated dissolution kinetics of tablets, pills, capsules, microparticles and suppositories.

Room temperature (r.t. or RT) or ambient temperature depicts a temperature in the range 20-25° C.; over night denotes a time period in the range 12-16 hours. Percentages are by weight, temperatures by degrees Celsius (centigrade) unless otherwise indicated. Abbreviations used in the examples or elsewhere:
ACN acetonitrile
API active pharmaceutic ingredient
BSA bovine serum albumin (Fluka)
IPA isopropanol
PO class I hydrophobin from *Pleurotus ostreatus,*
RT room temperature
SC class I hydrophobin from *Schizophyllum commune,*
SDS sodium dodecyl sulphate,
TR class II hydrophobin from *Trichoderma reesei,*
TT class I hydrophobin from *Talaromyces thermophilus,*

U enzyme unit,
w/v parts or percentage by weight relative to total volume (approximated density=1),
w/w parts or percentage by weight relative to total weight.

General Procedures

Preparation of Hydrophobins

Class I hydrophobins from *Schizophyllum commune* (SC), *Pleurotus ostreatus* (PO) and *Talaromyces thermophilus* (TT) and a class II hydrophobin from *Trichoderma reesei* (TR) are used for the purpose of the invention.

The protein sequences for said hydrophobins are obtained from NCBI/Gene Bank: SC: accession number P16933; PO: accession number CAA76494; TR: accession number CAA72636. Amino acid sequences are translated into nucleic acid sequences. For expression of TT, the nucleotide sequence is obtained from NCBI/Gene Bank with the accession number CS390617. After optimisation of codon usage towards *E. coli*, the cDNAs are synthesized (Sloning Bio-Technology, Pucheim, Germany). Hydrophobin nucleic acid sequences are cloned into a pET vector comprising T7-RNA-polymerase and a 6×his-tag sequence (pET15, Novagen) and transformed into the expression host *E. coli* BL21.

Fermentation of *E. coli* BL21 (DE3) transformed with expression vector comprising the optimised hydrophobin cDNA is performed in a 10 litre scale for 16 hours using ZYM-5052 medium (25 mM $Na_2HPO_4$, 25 mM $KH_2PO_4$, 50 mM $NH_4Cl$, 5 mM $Na_2SO_4$, 20 mM $MgSO_4$, 5 g/l glycerol, 0.5 g/l glucose, 2 g/l alpha-lactose monohydrate, 5 g/l yeast extract, and 10 g/l NZ-amines (purchased from Sigma)) in the presence of 100 µg/ml ampicillin or 25 µg/ml kanamycin, respectively. After harvest of the biomass, the sedimented cells are frozen in liquid nitrogen and stored at −80° C. After treatment of thawed aliquots of sedimented cells with sonication, the released inclusion bodies are solubilised by boiling the cell homogenate for 30 sec. and stirring for 2 h at 600 rpm at 20° C. Cell debris is sedimented by centrifugation for 10 min and the protein containing supernatant is passed through a filter with 0.22 µm. The filtrate is separated by affinity chromatography on nickel sepharose (GE Healthcare) and the eluted fractions are analysed on SDS polyacrylamide gel electrophoresis. The hydrophobin-containing fractions are cumulated and subsequently the hydrophobin-containing solution is desalted by dialysis in a Slide-A-Lyzer (Pierce) with a 10 kDa cut off membrane against water (30 ml eluate in 3 liters of water for 16 hours). The protein concentration is determined using a BCA assay (Pierce). The hydrophobin solution is quick-frozen in liquid nitrogen and lyophilised. For the use of the invention, aqueous solutions of hydrophobin containing 200 µg/ml protein are applied.

Filling of Capsules with Indicator Dye

For setting up the leakage experiments, gelatine capsules with a volume of 0.68 $cm^3$ (Capsulae operculatae Nr. 0, Pharmapol GmbH, D-25578 Dageling) are filled with the indicator dye bromo phenol blue. The capsules are filled with equal weight proportions of mannitol, sodium hydrogen carbonate, trisodium citrate dehydrogenate and water-soluble bromo phenol blue and closed by joining the upper and lower part of the capsule tightly. To avoid unspecific leakage from the capsule, the joint is sealed.

Coating of Capsules with Hydrophobins

The filled and sealed capsules are sprayed using a commercially available nebuliser with a solution of 200 μg/ml SC in water. For control experiments, capsules are sprayed with 200 μg/ml BSA in water with 0.002% w/v sodium dodecyl sulfate (SDS) or only with water containing 0.002% w/v SDS.

Coating of Capsules with a Biopolymer Consisting of Alginate and Hydrophobins

Filled and sealed capsules were submerged in a solution of 2% w/v alginate (E400) containing 200 μg/ml hydrophobin for 10 seconds. For control experiments, capsules are submerged in a solution of 200 μg/ml BSA containing 0.002% w/v SDS. Crosslinking of alginate is accomplished by subsequent submerging in 0.1 M $CaCl_2$. Subsequently, the capsules are dried at room temperature.

Evaluation of Release Properties

For testing the release of dye from the capsules after different surface treatments, the capsules are submerged in 50 ml 0.1 M HCl corresponding to a pH of 1.0 in order to mimic the acidic environment in the stomach. In a second setup, 0.4 U/ml pepsin are added to the 0.1 M HCl to test for resistance to a typical enzyme in the stomach juice. Quantification of the release is accomplished by computer aided optical evaluation of different areas of the solution in the immersion bath leading to arbitrary luminance units.

Coating of Tablets

Homeopathic Traumeel®S tablets (Heel GmbH, Baden Baden, Germany) are used for coating experiments. These tablets are highly soluble and are formulated based on lactose monohydrate and magnesium stearate. Tablets are immersed in a solution of 2% alginate comprising 200 μg/ml SC, TT or BSA as control, respectively. Tablets are then immersed immediately into a solution of 0.1 M $CaCl_2$ and dried at room temperature. For the dissolution test, tablets are immersed in 50 ml 0.1 M HCl at room temperature.

EXAMPLE 1

Release from Gelatine Capsules with or without Hydrophobin Coating

The release of dye from capsules coated by spraying with hydrophobins or as a control with water, respectively, is assayed in an acidic environment to mimic stomach conditions. The amount of dye contained in the immersion bath is measured by optical evaluation and given as arbitrary luminance units.

As FIG. 1A shows, the coating of the gelatine capsule with hydrophobin SC leads to a prolonged retention of dye within the capsule in an acidic environment within the interval of observation (2 hours). The same advantageous release characteristics are observed when the composition of gastric juices is simulated by addition of 0.4 U/ml pepsin to the liquid of the immersion bath (FIG. 1B).

Results: The assay depicted in FIG. 1 shows that the surface treatment of gelatine capsules by spraying with hydrophobins is a suitable method to modify the properties of this pharmaceutical form in beneficial way with regard to a potential use to achieve a retarded drug release.

EXAMPLE 2

Release from Gelatine Capsules Coated with Alginate with or without Admixture of Hydrophobin Hydrophobin SC is prepared and the gelatine capsules are filled with indicator dye as described above. Filled and sealed capsules are submerged in a solution of 2% w/v alginate (E400) containing 200 μg/ml hydrophobin. For control experiments, capsules are submerged in a solution of 200 μg/ml BSA containing 0.002% w/v SDS.

As can be observed in the assay depicted in FIG. 2A, the resistance of capsules treated with a polymer consisting of alginate with an admixture of hydrophobin to acidic conditions is comparable to that of gelatine capsules sprayed with hydrophobin for surface treatment (FIG. 1A). FIG. 2B shows that the retarded release characteristics of the capsules treated with the alginate/hydrophobin-biopolymer are essentially the same even when 0.4 U/ml pepsin are added to the liquid of the immersion bath containing 0.1 M HCl (pH 1.0) to test for resistance to a typical enzyme in the gastric juice. In contrast, the control capsules submersed in BSA become permeable much faster than observable in the immersion bath without pepsin.

Results: The admixture of hydrophobin to a solution of alginate yields a polymer solution which after submersion of the capsules confers similar properties as obtained by spraying with hydrophobin (example 1).

EXAMPLE 3

Release from Gelatine Capsules Coated with a Biopolymer Consisting of an Admixture of Alginate and Three Different Hydrophobins in Acidic, Neutral and Basic Environments Three hydrophobins are used to test if the modulation of the release kinetics of alginate coated gelatine capsules can be achieved with different hydrophobins. SC is prepared as described further above. Two additional hydrophobins are recombinantly produced in a similar procedure as described for SC. TT is from *Talaromyces thermophilus* and PO from *Pleurotus ostreatus*. Capsules are filled with indicator dye, sealed and immersed in a mixture of alginate and hydrophobin SC, TT or PO, respectively, as described in examples 1 and 2. As a control, an admixture of alginate and BSA is used. All proteins (hydrophobins and BSA) are applied in a concentration of 200 μg/ml (w/v).

To simulate the environment in stomach and intestine, acidic (pH 1.0, FIG. 3A) or basic (pH 12.0, FIG. 3C) conditions, respectively, are adjusted before submerging the capsules for the release assay. For comparison a neutral pH is also assayed (FIG. 3B).

Results: Each hydrophobin renders the capsules coated with the modified alginate resistant to an acidic and neutral environment in a comparable manner. The integrity of the capsules is maintained for a longer interval in an acidic than in a neutral environment. Control capsules show a faster onset of dye release as compared to hydrophobin treated capsules. In the immersion bath with a strongly basic pH, the onset of dye release is observed much earlier with all capsules (hydrophobin and control) as compared with the neutral and acidic environment. An increased resistance to stomach juices can be achieved especially with SC and TT. As can be observed in FIG. 3c, TT renders the capsules significantly more resistant to a basic environment than the other hydrophobins, which may be useful for the preparation of suppositories with a retarded drug release. All three hydrophobins change the leakage properties of the capsules in different environments.

EXAMPLE 4

Coating of Tablets and Pills with a Biopolymer Consisting of an Admixture of Alginate and Two Different Hydrophobins Traumeel® S (Heel) tablets are coated with hydrophobin, and resistance to acidic conditions of pH 1.0 is tested in a dissolution assay. Traumeel® S tablets are submersed in a solution of 2% alginate, containing 200 μg/ml TT, PO, TR or SC, respectively. As control, a solution of alginate containing 200 μg/ml BSA and 0.002% SDS is used. After short submersion, alginate-coated tablets are allowed to polymerise in 0.1M $CaCl_2$ and dried over night at ambient temperature.

The incubation for the dissolution test is at ambient temperature in 0.1M HCl for 10 to 120 min. Results: The coating of tablets with a biopolymer consisting of alginate with an admixture of hydrophobin yields beneficial properties regarding sustained release of a pharmaceutical composition. After incubation for 260 min at a pH of 1, a prolonged integrity of the tablets coated with the alginate/hydrophobin biopolymer is clearly observed, with the class I hydrophobins SC, TT and PO being superior to the class II hydrophobin TR with regard to resistance to dissolution of the coated tablet (FIG. 5A).

EXAMPLE 5

Matrix Formation and Increased Stability of Gelatine by Hydrophobin

Gelatine (stained red, purchased from RUF, Quakenbrück, Germany) is solubilized in water or a SC-solution (final concentration 200 μg/ml). 500 μl solubilized gelatine is added per well of a 6-well macroplate. Gelatine is dried over night at 50° C. Then 500 μl $H_2O$, 0.1 N HCl or 0.1 N HCl with 0.4 U/ml pepsin, respectively, are added to the wells. The optical evaluation of the wells is shown in FIG. 5B.

Results:

Without hydrophobin, the gelatine is completely dissolved, whereas SC3 inhibits the dissolution of gelatine. Similar results are obtained for POH3 and TT1 (not shown). The results show that the dissolution of the biopolymer gelatine in water is strongly hampered and also in an environment mimicking gastric juices the dissolution is reduced. Gelatine with hydrophobin appears to form a matrix-like structure (FIG. 5B).

conclusions

Different class I and II hydrophobins are used to investigate the integrity of specimen used for pharmaceutical purposes after bringing into contact the specimen with a hydrophobin solution or a biopolymer consisting—by way of example—of gelatine and/or alginate with an admixture of at least one hydrophobin. It is the surprising finding of the invention, that use of hydrophobins as galenic excipients can modulate the characteristics of pharmaceutical forms in an advantageous way. Bringing into contact a specimen with class I hydrophobins used in the present invention renders the pharmaceutical form (exemplified for capsules and tablets) more robust to gastric juice as compared to coating with alginate only or as admixture with BSA. The admixture of a hydrophobin to a solution of alginate yields a biopolymer solution which after submersion of the capsules confers similar properties as obtained by coating with hydrophobin by spraying, showing that both the surface treatment and the modification of a pharmaceutically acceptable polymer or carrier are potential uses of hydrophobins as galenic excipients according to the invention. It is also shown by example that distinct characteristics of different hydrophobins occur in environments of acidic, neutral and basic pH, allowing for the preparation of a galenic form of desired drug release characteristics by selection of a suitable hydrophobin.

The present invention therefore provides a means for the modulation of galenic forms in terms of stability—i.e. resistance to disintegration, matrix formation—, pH-dependence and drug release kinetics. According to the non-limiting examples, the invention provides an application for the preparation of galenic forms to achieve a desired release characteristic of drugs during the passage through the body depending on the route of application of the pharmaceutical composition. Hydrophobin can be potentially used to either stabilise pharmaceutically relevant polymers or to generate matrices with polymeric compounds, e.g. for the production of improved matrix tablets.

Figure 1:
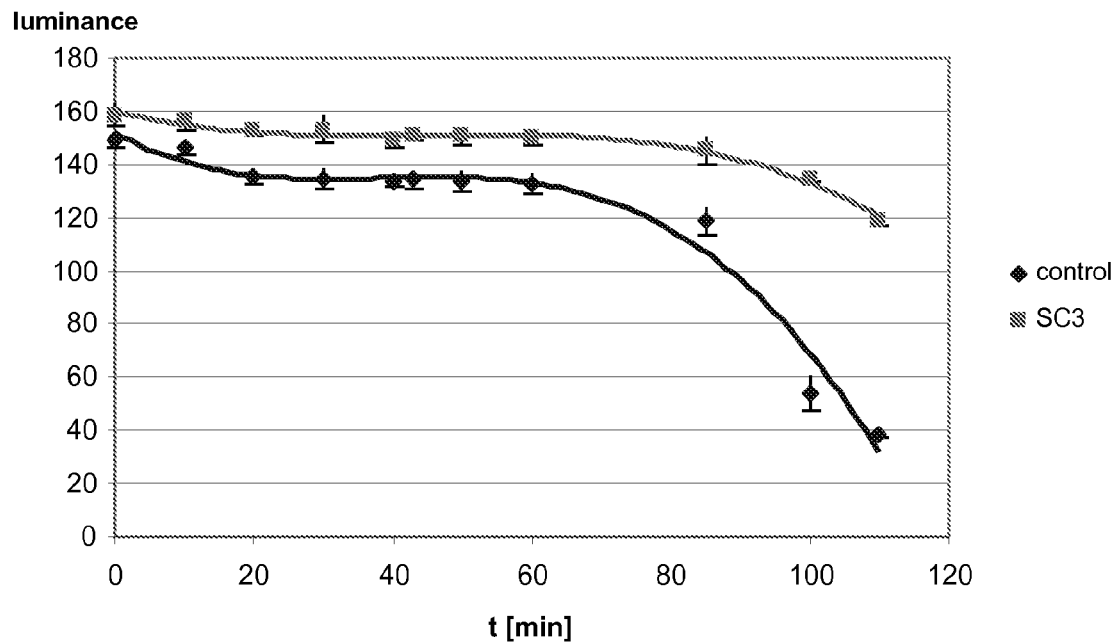
FIG. 1: Diffusion and/or leakage from gelatine capsules filled with indicator dye coated by spraying with hydrophobin SC3 or water. Capsules are submerged in water with pH 1.0, with (B) or without (A) presence of pepsin. Release of bromo phenol blue from the capsules is determined as luminance of the water by colorimetric evaluation and plotted versus time of incubation. Hydrophobin coating renders capsules resistant to an acidic environment.
Figure 1:
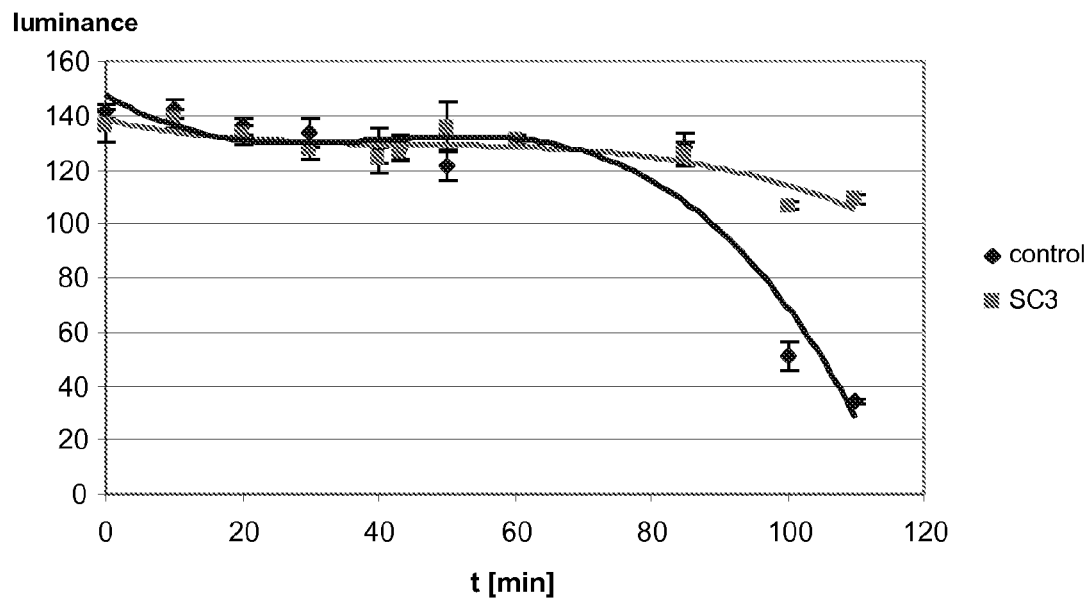
Figure 2:
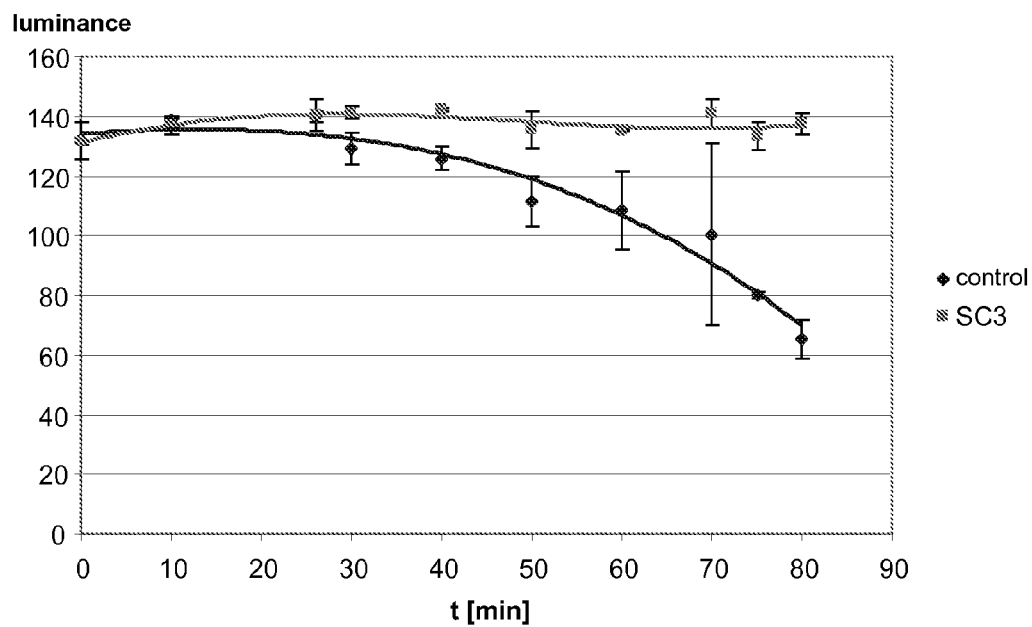
FIG. 2: Diffusion and/or leakage from gelatine capsules filled with indicator dye coated by submerging into an alginate-solution containing hydrophobin SC3 or BSA (control), respectively, at pH 1.0 (A) or at pH 1.0 with 0.4 U/ml pepsin (B). Evaluation is done as described under FIG. 1.
Figure 2:
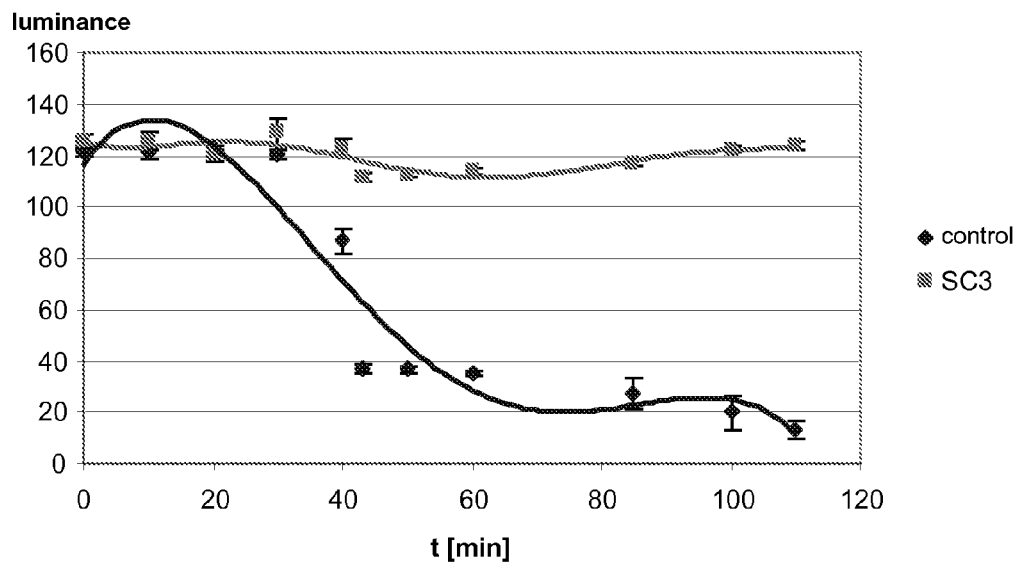
Figure 3:
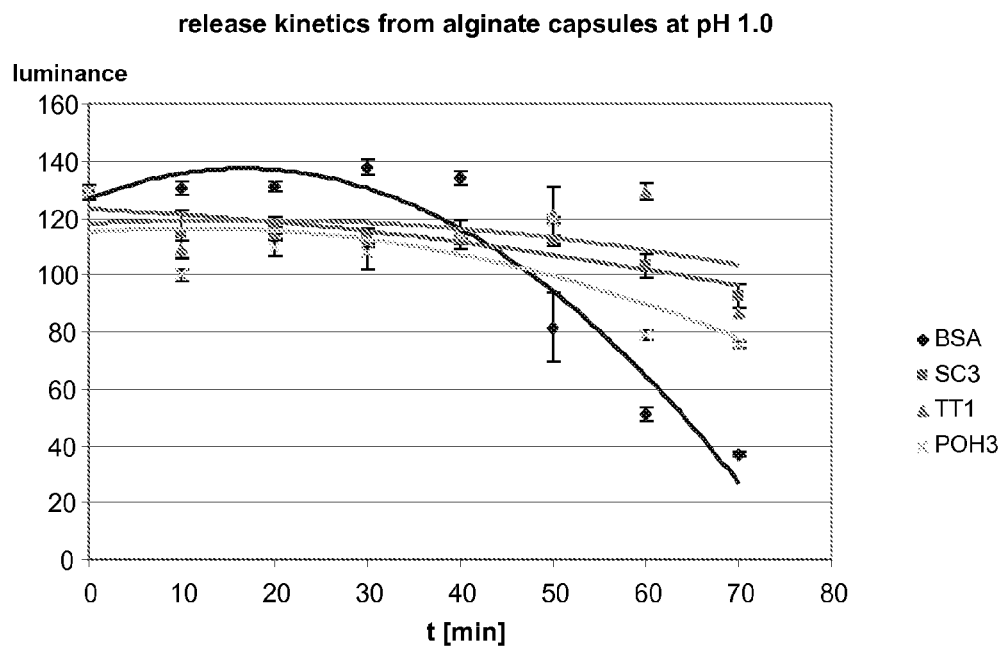
FIG. 3: Diffusion and/or leakage from gelatine capsules filled with indicator dye coated by submerging into an alginate-solution containing the hydrophobins SC3, TT1, POH3 or BSA, respectively, in an acidic (A, imitating stomach), neutral (B) or basic (C, imitating intestine) environment. Evaluation is done as described under FIG. 1.
Figure 3:
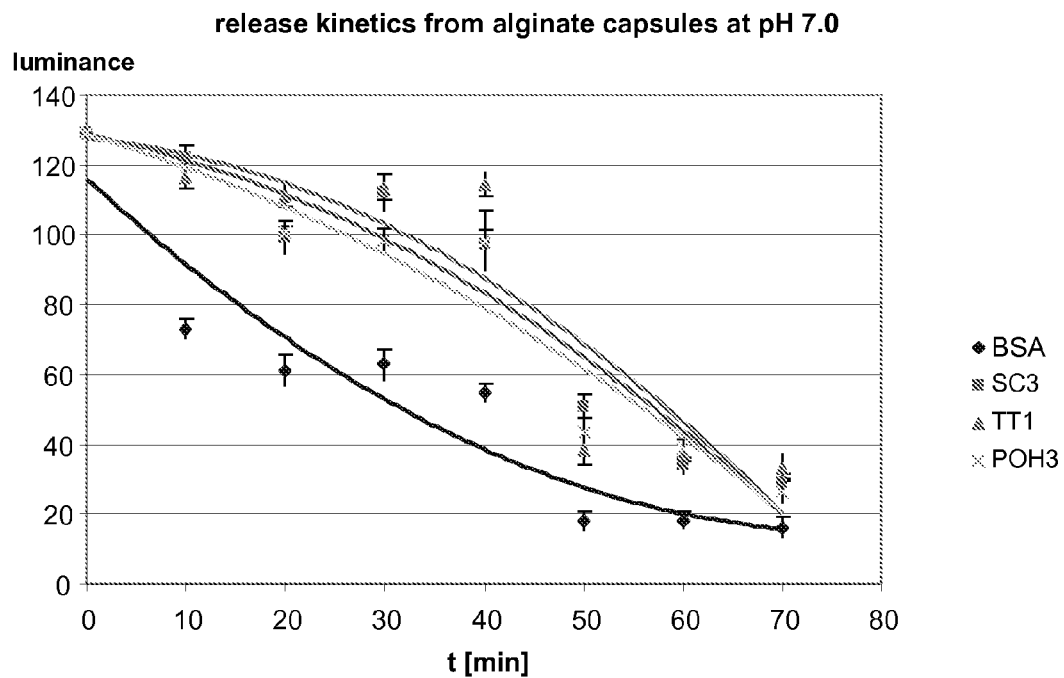
Figure 4:
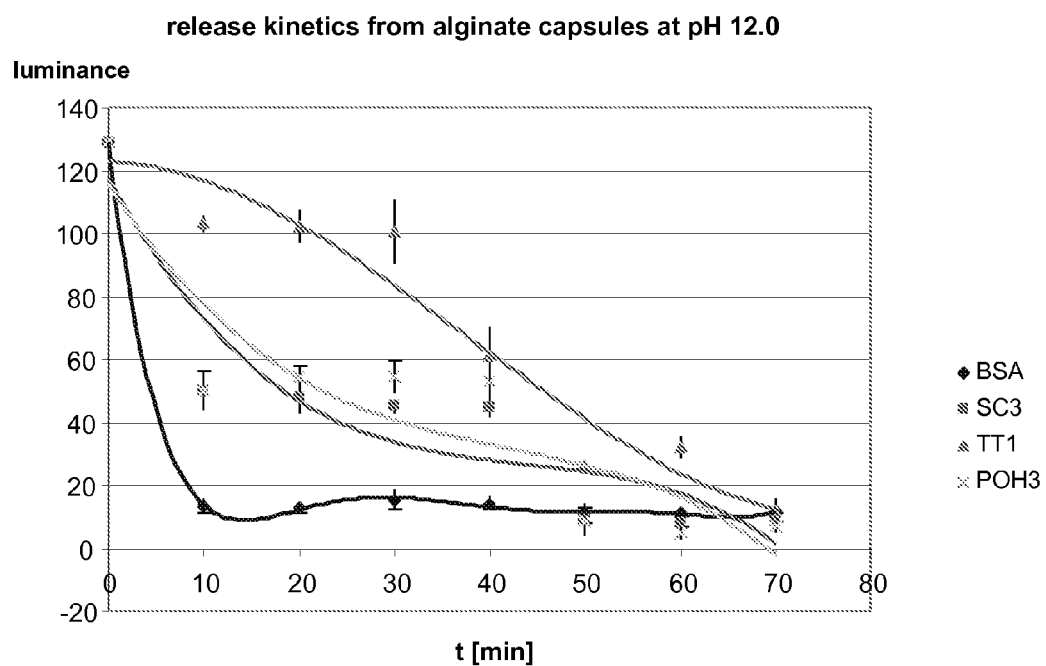
FIG. 4: Relative change of water contact angle of a 1% b.w. protein solution on a polypropylene plate (Borealis HC115MO) compared to pure water, demonstrating high amphiphilicity of hydrophobins.
Figure 4:
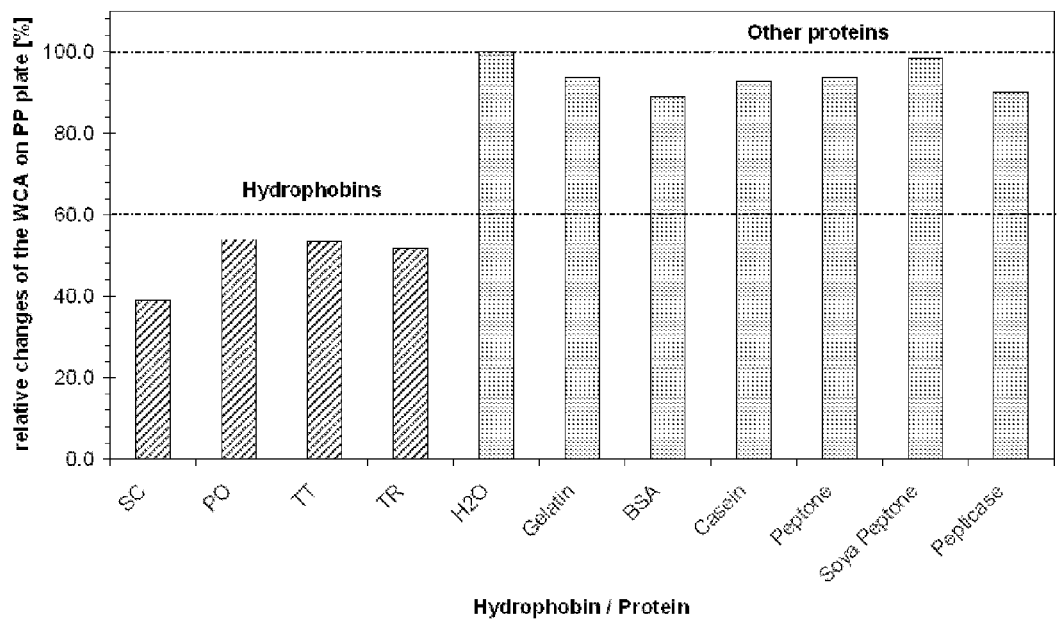
Figure 5:
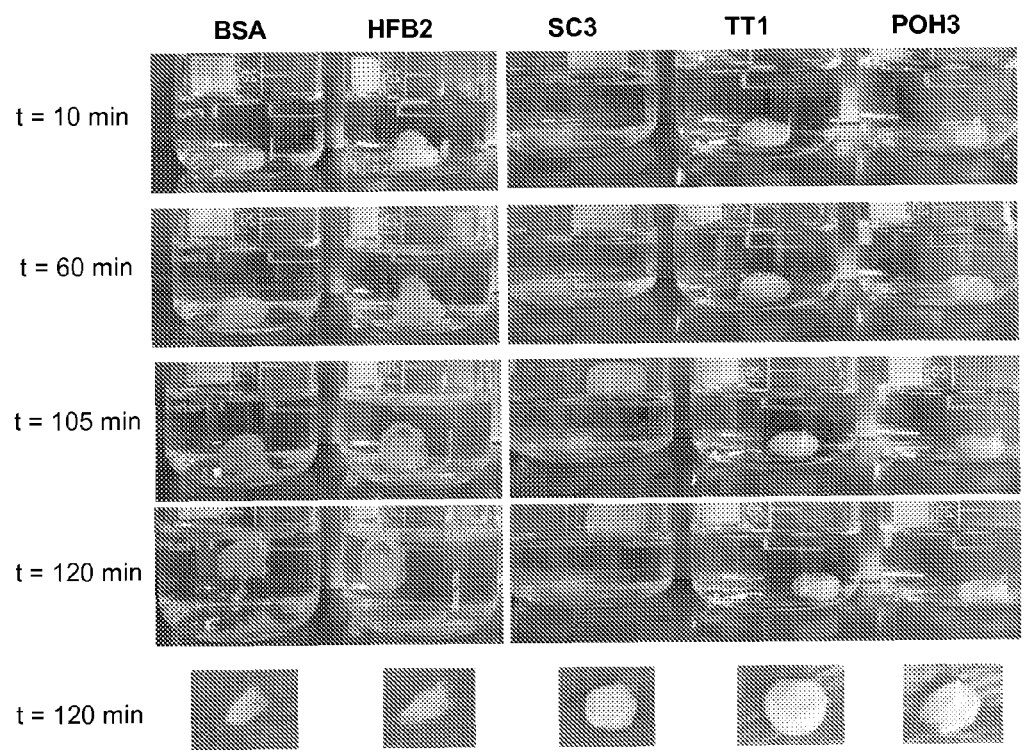
FIG. 5: A: Dissolution of tablets in an acidic solution of pH 1.0 for a time period of 10 to 120 minutes. Tablets were previously coated by submersion in an alginate-solution containing either hydrophobins HFB2 or SC3 or TT1 or POH3 or, as a control, BSA. Coating with hydrophobin, especially SC3, delays the dissolution of the tablets significantly.
Figure 5:
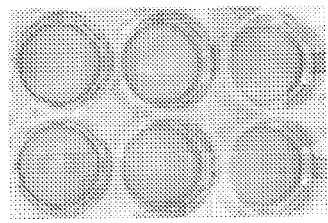
Figure 5:
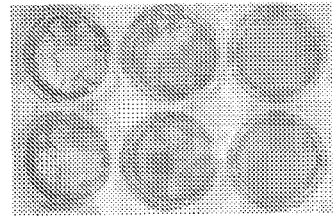

B: Gelatin films (left) and gelatin films containing hydrophobin (right) contacted with water, 0.1 N aq. HCl and 0.1 N HCl containing pepsin (equal time periods); films containing hydrophobin show a distinctly slower dissolution rate.

The invention claimed is:

1. A method for the preparation of a pharmaceutical composition comprising a solid form of a medicament with modulated release characteristics in vivo,
which method comprises incorporating a surface active protein selected from hydrophobins into said solid form, or coating said solid form with said surface active protein,
where the solid form is selected from the group consisting of capsules, multi capsules, pills, tablets, matrix tablets, multilayer tablets, coated tablets, microgranules and suppositories.

2. A pharmaceutical composition comprising a solid form of a medicament,
wherein a surface active protein selected from hydrophobins is contained in a coating on the outer surface of the solid form or is incorporated into a matrix material forming an outer surface of the solid form,
where the solid form is selected from the group consisting of capsules, multi capsules, pills, tablets, matrix tablets, multilayer tablets, coated tablets, microgranules and suppositories.

3. A method according to claim 1, wherein the surface active protein is characterized in that a 1% b.w. aqueous solution or dispersion thereof lowers the contact angle on a polypropylene surface by 20 degrees or more relative to pure water.

4. A method according to claim 3 wherein the surface active protein is a class II hydrophobin.

5. A method according to claim 1, wherein the solid form is selected from capsules, multi capsules, pills, tablets, matrix tablets, multilayer tablets, microgranules and suppositories.

6. A method according to claim 1 where the solid form further comprises one or more pharmaceutically acceptable ingredients selected from surface active agents, binders, biopolymers, flow aids, lubricants, disintegrants, sweeteners, flavours and colorants.

7. A method according to claim 1, wherein an aqueous solution or dispersion of the surface active protein is coated onto the solid in an amount from 0.001 to 1000 µg per gram of the final solid form.

8. A method according to claim 1, wherein the surface active protein is an aqueous solution with concentration of the surface active protein of 0.01 to 10.0 mg/ml.

9. A composition according to claim 2, wherein the surface active protein is characterized in that a 1% b.w. aqueous solution or dispersion thereof lowers the contact angle on a polypropylene surface by 20 degrees or more relative to pure water.

10. A composition according to claim 9 wherein the surface active protein is a class II hydrophobin.

11. A composition according to claim 2, wherein the solid form is selected from the group consisting of capsules, multi capsules, pills, tablets, matrix tablets, multilayer tablets, microgranules and suppositories.

12. A composition according to claim 2 wherein the solid form further comprises one or more pharmaceutically acceptable ingredients selected from surface active agents, binders, biopolymers, flow aids, lubricants, disintegrants, sweeteners, flavours and colorants.

13. A method according to claim 3 wherein the surface active protein is a class I hydrophobin.

14. A composition according to claim 9 wherein the surface active protein is a class I hydrophobin.

* * * * *